United States Patent
Jiang

(10) Patent No.: US 7,139,366 B1
(45) Date of Patent: Nov. 21, 2006

(54) TWO-DIMENSIONAL SMALL ANGLE X-RAY SCATTERING CAMERA

(75) Inventor: Licai Jiang, Rochester Hills, MI (US)

(73) Assignee: Osmic, Inc., Auburn Hills, MI (US)

( * ) Notice: Subject to any disclaimer, the term of this patent is extended or adjusted under 35 U.S.C. 154(b) by 0 days.

(21) Appl. No.: 11/142,862

(22) Filed: May 31, 2005

(51) Int. Cl.
*G01N 23/201* (2006.01)
(52) U.S. Cl. .......................................... 378/88; 378/86
(58) Field of Classification Search ............ 378/83–90, 378/57, 80, 73, 78
See application file for complete search history.

(56) References Cited

U.S. PATENT DOCUMENTS

| | | | |
|---|---|---|---|
| 4,749,562 A | 6/1988 | Lane et al. | |
| 4,751,722 A | 6/1988 | Harding et al. | |
| 4,956,856 A | 9/1990 | Harding | |
| 5,016,267 A | 5/1991 | Wilkins | |
| 5,028,352 A | 7/1991 | Hietala et al. | |
| 5,619,548 A | 4/1997 | Koppel | |
| 6,014,423 A | 1/2000 | Gutman et al. | |
| 6,041,099 A | 3/2000 | Gutman et al. | |
| 6,054,712 A | 4/2000 | Komardin et al. | |
| 6,175,117 B1 | 1/2001 | Komardin et al. | |
| 6,196,715 B1 | 3/2001 | Nambu et al. | |
| 6,330,301 B1 | 12/2001 | Jiang | |
| 6,459,761 B1 * | 10/2002 | Grodzins et al. | 378/57 |
| 6,483,891 B1 | 11/2002 | Lazarev et al. | |
| 2003/0016783 A1 * | 1/2003 | Grodzins et al. | 378/57 |

FOREIGN PATENT DOCUMENTS

EP  1 477 796 A2  11/2004

OTHER PUBLICATIONS

A Small Angle X-Ray Scattering Study of the Effect of Pressure on the Aggregation of Asphaltene Fractions in Petroleum Fluids under Near-Critical Solvent Conditions, N.F. Carnahan, L. Quintero, D.M. Pfund, J.L. Fulton, R.D. Smith, M. Capel, K. Leontaritis, 1993, American Chemical Society, pp. 2035-2044.
Construction of a Small-Angle X-Ray Scattering Diffractometer for the Study of Fluctuations in Solutions, Hisashi Hayashi, Kelko Nishidawa and Takae Iijima, Japanese Journal of Applied Physics, vol. 28, No. 8, Aug. 1989, pp. 1501-1503.

(Continued)

*Primary Examiner*—Edward J. Glick
*Assistant Examiner*—Hoon Song
(74) *Attorney, Agent, or Firm*—Brinks Hofer Gilson & Lione

(57) ABSTRACT

A two-dimensional x-ray scattering camera includes a source, an optic, a detector, and a pair of collimating blocks. The source emits x-ray beams that are reflected by the optic towards a sample. The detector detects scattering from the sample, the pair of collimating blocks is positioned between the optic and the detector to collimate the beam. A bottom surface of one block is substantially parallel a top surface of the other block, and the blocks are rotatable relative to the beam about a pivot. The system forms a two-dimensional beam that is symmetric about the primary beam axis at the detector position, regardless how the beam is collimated by the collimating blocks. The system therefore eliminates smearing and can be used for anisotropic small angle scattering at high resolution and low $Q_{min}$.

15 Claims, 5 Drawing Sheets

OTHER PUBLICATIONS

Two approaches for irradiating cells individually: a charged-particle microbeam and a soft X-ray microprobe; M. Folkard, B. Vojnovic, G. Schettino, M. Forsberg, G. Bowey, K. M. Prise, B.D. Michael, A.G. Michette, S.J. Pfauntsch; Nuclear Instruments and Methods in Physics Research B 130 (1997) pp. 270-274.

Characterization of pore distribution in activated carbon fibers by microbeam small angle X-ray scattering; D. Loznano-Castello, E.Raymund- Pinero, D. Cazorla-Amoros, A.Linares-Solano, M. Muller, C. Riekel, 2002 Elsevier Science Ltd., Carbon 40 (2002) pp. 2727-2735.

Apparatus for simultaneous observation of the electro-optic response and small angle x-ray scattering in liquid crystals; H.F. Gleeson, C. Carboni and A.S. Morse; American Institute of Physics, 1995, pp. 3563-3568.

PIXE setup for liquid sample analysis, J. Kral, J. Voltr, Z. Nejedly; Nuclear Instruments and Methods in Physics Research B 109/110 (1996) pp. 167-169.

Small-Angle X-Ray Scattering Study of Polyelectrolyte Solutions; M. Tomsic, M. Bester Rogac and A. Jamnik; Acta Chism. Slov. 2001, 48, pp. 333-342.

Small Angle X-Ray Scattering; O. Glatter and O. Kratkey; London; New York: Academic Press, 1982, pp. 53-83 and pp. 85-117.

* cited by examiner

TWO-DIMENSIONAL SMALL ANGLE X-RAY SCATTERING CAMERA

BACKGROUND

The present invention relates generally to an x-ray scattering camera, and more particularly relates to a two-dimensional x-ray scattering camera.

In x-ray scattering, the performance of the camera is typically characterized by the flux, the resolution, defined as the beam diameter at the detector position divided by the sample-to-detector distance, and a parameter $Q_{min}$, defined as $$Q_{min} = \frac{4\pi}{\lambda} \sin\theta_{min},$$

where $\lambda$ is the wavelength and $\theta_{min}$ is the minimum access angle (i.e., the smallest angle, relative to the primary beam, at which meaningful scattering can be collected). In general, increasing the resolution of the system decreases the flux and $Q_{min}$, whereas increasing the flux decreases the resolution and $Q_{min}$.

To address these issues, a camera known as a Kratky camera using a collimation block and an x-ray source in a line projection was developed. The Kratky camera has achieved high resolution, good flux and $Q_{min}$, but it is a one-dimensional camera and therefore suffers from smearing. Although many de-smearing procedures have been developed, some amount of information is still unavoidably lost. Moreover, because of its one-dimensional nature, the Kratky camera can be used only for isotropic samples. The pinhole camera, such as three-pinhole systems, were developed to overcome some of the shortcomings of the Kratky camera. The pinhole camera eliminates the lateral smearing caused by a one-dimensional beam, and can be used to investigate anisotropic samples. However, the pinhole camera has a low flux, low resolution, and its $Q_{min}$ is limited to about 0.005 Å$^{-1}$. In sum, the fundamental limitations of each type of camera have not been overcome: the Kratky camera cannot be used for investigating anisotropic samples, and the pinhole camera cannot achieve a very high resolution and low $Q_{min}$.

From the above, it is seen that there exists a need for an improved two-dimensional camera with high resolution and low $Q_{min}$.

BRIEF SUMMARY

A two-dimensional x-ray scattering camera includes a source, an optic, a detector, and a pair of collimating blocks. The source emits x-ray beams that are reflected by the optic towards a sample. The detector detects scattering from the sample, the pair of collimating blocks is positioned between the optic and the detector to collimate the beam. The bottom surface of one block is substantially parallel to the top surface of the other block, and the blocks are rotable relative to the beam about a pivot.

A particular feature of this system is that the beam intensity distribution at the detector position is independent of the block collimation, which by nature is asymmetric. Such a beam can be formed by using a two-dimensional multilayer optic (μCMF) and a microfocusing source. The combination of these two elements (block collimation and the highly defined two-dimentional beam) offers a camera with a low $Q_{min}$ and high resolution.

Some embodiments of the invention may have one or more of the following advantages. The camera can be used to investigate anisotropic material and can be configured into a high resolution reflectometer, or a high resolution reflective SAXS camera. Since the sample-to-detector distance is not necessarily as long as in the pinhole camera case, the camera has a large angular range and may make it possible to use the camera in wide angle scattering.

Further advantages and features of the invention will become apparent from the following detailed description and from the claims.

BRIEF DESCRIPTION OF THE DRAWINGS

The accompanying drawings, incorporated in and forming a part of the specification, illustrate several aspects of the present invention and, together with the description, serve to explain the principles of the invention. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

Figure 1:
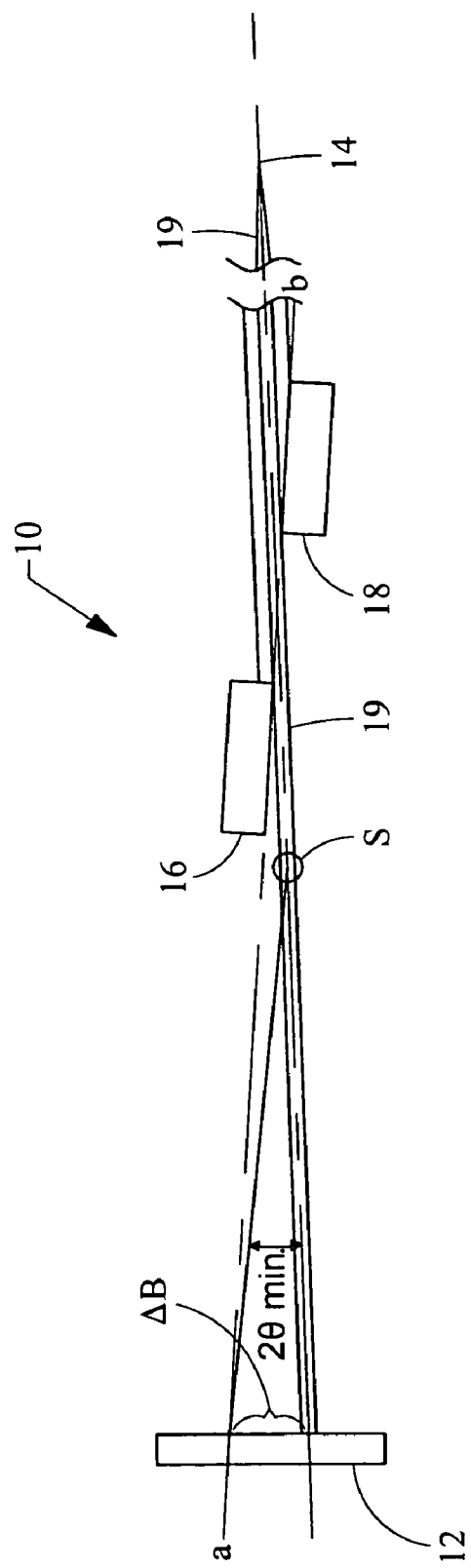
FIG. 1 is a schematic illustration of a Kratky camera.

FIG. 1 depicts a Kratky camera 10 commonly used for small angle x-ray scattering. The camera 10 includes a detector 12 and an x-ray source 14. The x-ray source 14 is a one dimensional line source. X-rays are collimated by a pair of blocks 16 and 18 aligned in a common plane (i.e. the plane of the paper). The collimation blocks direct x-rays 19 at a sample (S), the scattering of which is captured by the detector 12. When the two blocks 16 and 18 are properly aligned, there is no parasitic scattering beyond the line extending between the points a-b.

A Ni filter can be employed to suppress Kβ radiation and soft continuous x-rays. The Kratky camera 10 has good flux and $Q_{min}$ but the one-dimensional nature of the Kratky camera 10 makes it suitable for use with only isotropic samples. Moreover, the Kratky camera produces a scattered x-ray pattern that suffers from severe distortion know as smearing. Although many de-smearing routines have been proposed and implemented, some information is unavoidably lost, and therefore, the resolution, in particular, Δd/d, where Δd is the smallest resolvable d-spacing at the specific d, is compromised.

Recently, Kratky cameras have employed focusing multilayer optics that enhances the performance of the camera. For example, the flux can be increased by a factor of about forty with the use of multilayer optics. Moreover, the background noise caused by Kβ and Bremsstrahlung radiation is removed, and the resolution, which can be measured by the beam width at the detector (ΔB) divided by the distance between the sample and the detector (SD), is improved because of the enhanced focusing capabilities of the optics. Nonetheless, the one-dimensional nature and the smearing problems associated with the Kratky camera remain.

Figure 2:
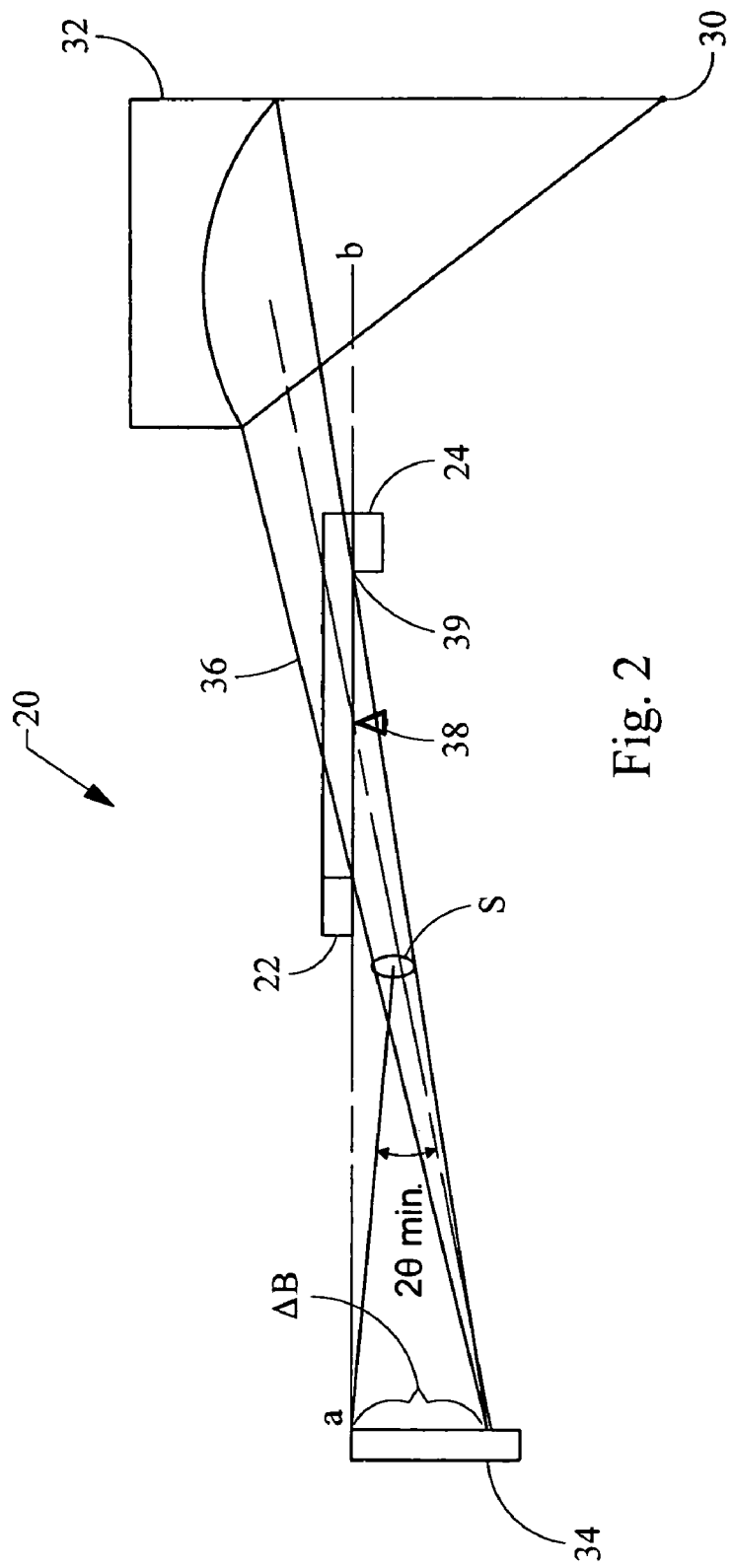
FIG. 2 is a schematic illustration of a camera with a two-dimensional x-ray source in accordance with the invention.
Figure 3:
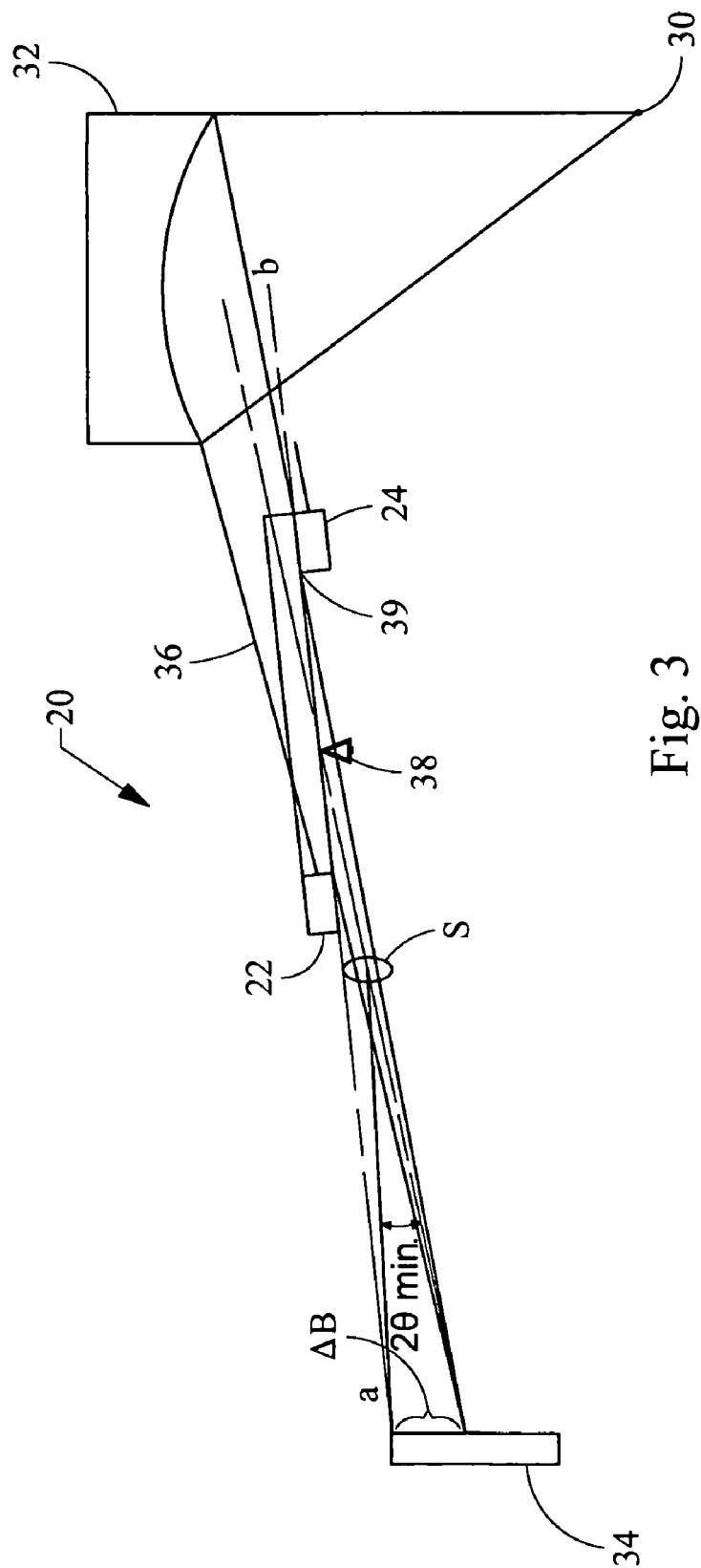
FIG. 3 is a schematic illustration of the collimation blocks rotated about a pivot to adjust the camera's resolution and $Q_{min}$.
Figure 4:
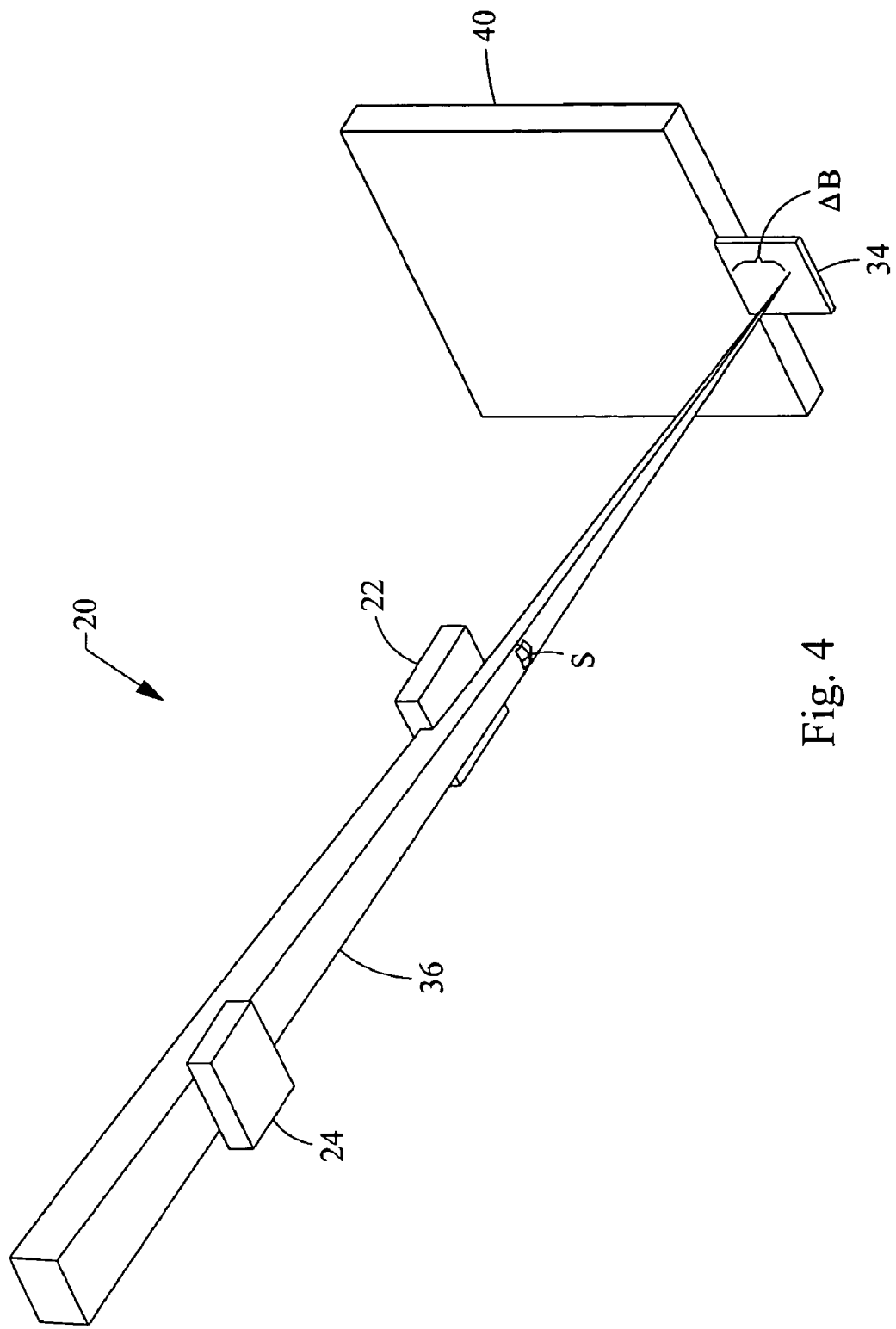
FIG. 4 is a perspective view of a portion of the camera shown in FIGS. 2 and 3.

Referring now to FIGS. 2, 3, and 4, a two-dimensional camera 20 includes a pair of collimating blocks 22 and 24, a microfocusing source 30 and an optic 32, such as a two-dimensional multi-layer optic (or μCMF optic) in accordance with the invention. The optic 32 can be of the type described in U.S. Pat. No. 6,041,099 or U.S. Pat. No. 6,014,423, the entire contents of which are incorporated herein by reference. The combination of the microfocusing source 30 and the optic 32 produces a well defined two-dimensional beam 36. The two-dimensional beam 36 with the collimating blocks 22 and 24 provides a camera with high resolution and low $Q_{min}$. The camera 20 has exceptional resolution (i.e. good Δd/d) and angular range ($Q_{min}$ from 0.0003 Å$^{-1}$ to wide angles). The flux from the camera 20 is higher than a system with a rotating anode generator and a CMF optic for the same $Q_{min}$. The $Q_{min}$-range can be easily and continuously changed by rotating the collimating blocks 22 and 24 about, for example, a pivot 38, and moving a beam stop 34 positioned below a detector 40 (FIG. 4) away and towards the detector. Note that in some implementations, the rotation of the collimating blocks 22 and 24 can be about another position, such as edge 39 of the block 24. Note also that the beam stop 34 and detector 40 do not have to rotate with the collimating blocks 22 and 24. Because of the small angular variations, the position of the detector 40 can be fixed without any repositioning, and the position of the beam stop 34 is adjusted to block parasitic scattering or to allow access to a smaller angular zone.

The collimating blocks 22 and 24 offer a parasitic-scattering-free zone above the a-b line identified in FIGS. 2 and 3. Since the beam 36 is well defined and symmetric about the primary beam direction, the scattering pattern is two-dimensional in nature. The beam is symmetric because the deviation of the beam from being focused is determined by the source intensity distribution, which can be considered as symmetric about the primary beam axis. If the beam 36 is a focusing beam and the detector 40 is at the focal point of the optic 40, a high resolution (i.e., small ΔB/SD) can be achieved. Since the spot size of the beam 36 at the detector 40 is mainly determined by the deviation from the ideal focusing, which is in turn caused by the non-point like source, the beam shape at the location of the detector 40 is not affected by the position of the collimating blocks 22 and 24. In other words, the beam shape at the detector 40 does not depend on the setting of a desired $Q_{min}$. The beam 36 at the location of the sample S can be sliced into a rectangular shape, while the shape of the beam as projected onto the plane of the detector 40 remains round. This assures that the scattering pattern is free of distortion from the collimation. Although a "half field" view is adequate for measurements of isotropic samples, for an anisotropic sample, a mechanism may be used to rotate the sample S to acquire data over the 360° field of view.

For example, to study an anisotropic sample, the sample S can be mounted to a stage integrated with the camera 20 so that the stage rotates the sample S about the longitudinal axis of the primary beam 36, enabling the investigator to obtain a complete scattering pattern. The flux of the camera 20 is at least a few times higher, and hence the total integration time is lower, than that of a pinhole camera.

As illustrated in FIG. 3, the $Q_{min}$ can be easily adjusted by rocking the collimating system of blocks 22 and 24 about the pivot 38 at the center of the collimating system. As mentioned above, the rotational center can also be at a corner of one of the collimating blocks. Unlike in a three pinhole system, the beam stopper 34 can also be adjusted by moving it relative to the detector 34.

In contrast to a pinhole camera, the camera 20 provides a much lower $Q_{min}$ range. The $Q_{min}$ can easily reach about 0.0003 Å$^{-1}$, equivalent to a $d_{max}$ (i.e. the maximum resolvable d-spacing) of about 2000 Å angstroms. In contrast, the pinhole camera can achieve a $d_{max}$ of about 1000 with an acceptable flux, which is a distinct disadvantaged compared to the camera 20. In addition, unlike the Kratky camera, the flux of the camera 20 does not decrease as $1/r^2$, where r is the distance between the source and detector. Therefore, the effective length of the camera 20 can be longer than that of the traditional Kratky camera. This longer length improves both the $Q_{min}$ and the resolution ΔB/SD.

Among other advantages, the camera system 20 is very flexible and easy to use. A small detector can be positioned in front of the beam stop 34 (the sample side) to measure the intensity of the primary beam and the absorption of the sample. The angular range can be extended easily for wide angle scattering. Moreover, Δd/d is proportional to ΔB/SD, and the small size of a microfocusing source offers superior resolution. In addition, the spot size of the microfocusing source, such as a Bede Scientific's MicroSource™, a company in the United Kingdom, can be adjusted to improve the resolution further.

The camera 20 is quite appropriate for use in medical small angle x-ray scattering, allowing the observation of first order peaks around 900 Å. With parallel beam optics, the camera 20 is quite suitable for use as a reflectometer. The camera 20 can be used in reflective small angle x-ray scattering in surface analysis, such as performed, for example, in semiconductor metrology.

Figure 5:
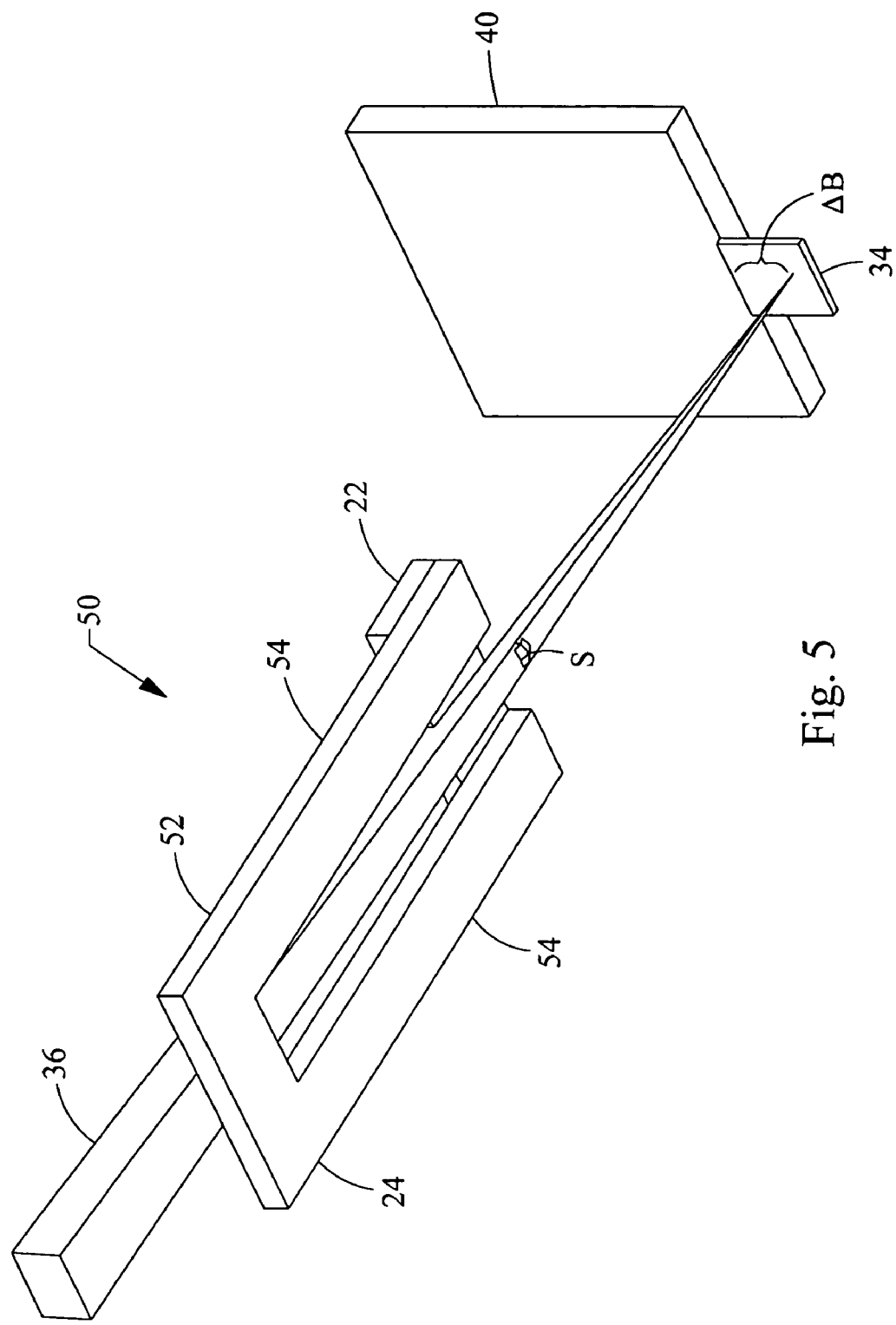
FIG. 5 is an alternative embodiment of a camera with a two-dimensional x-ray source in accordance with the invention.

The blocks 22 and 24 may be integrated as a single unit. For example, an implementation of a two-dimensional camera 50 shown in FIG. 5 includes a U-shaped structure 52 with a top portion that functions as one of the collimating blocks 24. The other collimating block 22 is mounted to the top of the legs 54 of the structure 52 so that the two blocks 22 and 24 are naturally aligned. Alternatively, the block 22 can be a portion of a U-shaped structure, and the block 24 is mounted to it.

Other embodiments are within the scope of the following claims. For example, the beam can be conditioned by forming a two-dimensional beam, enhancing flux and decreasing divergence by collimating or focusing the beam, or monochromatizing the beam to improve its spectrum, or any combination of the foregoing.

What is claimed is:

1. A two-dimensional x-ray scattering camera for analyzing a sample comprising:
   a source which emits x-rays;
   a two-dimensional optic which conditions the beam from the source to the sample;
   a detector which detects scattering from the sample; and
   a pair of collimating blocks positioned between the optic and the detector to collimate the beam and the sample being positioned between the source and the collimating blocks, a bottom surface of one block being substantially parallel to a top surface of the other block, the blocks being rotatable relative to the beam about a pivot.

2. The camera of claim 1 wherein the pivot is located between the pair of collimating blocks.

3. The camera of claim 1 wherein the pivot is located at an edge of one of the collimating blocks.

4. The camera of claim 1 wherein the optic is located between the collimating blocks and the source.

5. The camera of claim 1 wherein the blocks are two separate structures.

6. The camera of claim 1 wherein the blocks are a single integrated unit.

7. The camera of claim 1 further comprising a beam stop, the beam being focused at the detector.

8. The camera of claim 1 wherein the beam is conditioned by forming a two-dimensional beam, enhancing flux and decreasing divergence by collimating or focusing the beam, or monochromatizing the beam to improve its spectrum, or any combination of the foregoing.

9. A method of analyzing a sample with a two-dimensional x-ray beam comprising:

emitting x-rays from a source;

reflecting the beam from the source to the sample in two-dimensions with an optic;

collimating the beam with a pair of collimating blocks positioned between the source and the detector, the sample being positioned between the collimating blocks and the source, the blocks being rotatable relative to the beam about a pivot; and detecting scattering from the sample with a detector.

10. The method of claim 9 wherein the pivot is located between the pair of collimating blocks.

11. The method of claim 9 wherein the pivot is located at an edge of one of the collimating blocks.

12. The method of claim 9 wherein the optic is located between the collimating blocks and the source.

13. The method of claim 9 wherein the blocks are two separate structures.

14. The method of claim 9 wherein the blocks are a single integrated unit.

15. The method of claim 9 further comprising focusing the beam at detector.

* * * * *